United States Patent
Qian et al.

(10) Patent No.: US 12,066,425 B2
(45) Date of Patent: Aug. 20, 2024

(54) SENSOR ARRAY AND APPARATUS FOR SIMULTANEOUS OBSERVATION OF TISSUE ELECTROPHYSIOLOGY, CONTRACTILITY, AND GROWTH

(71) Applicant: Lawrence Livermore National Security, LLC, Livermore, CA (US)

(72) Inventors: Fang Qian, Santa Cruz, CA (US); Chao Huang, San Jose, CA (US); Anna Nikolaevna Ivanovskaya, Mountain View, CA (US); Kris Kulp, Livermore, CA (US); Elizabeth K. Wheeler, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 599 days.

(21) Appl. No.: 17/144,008

(22) Filed: Jan. 7, 2021

(65) Prior Publication Data
US 2021/0199638 A1    Jul. 1, 2021

Related U.S. Application Data

(62) Division of application No. 15/901,766, filed on Feb. 21, 2018, now Pat. No. 10,914,722.

(60) Provisional application No. 62/463,534, filed on Feb. 24, 2017.

(51) Int. Cl.
*G01N 33/483* (2006.01)
*C12M 1/34* (2006.01)
*C12M 1/42* (2006.01)
*C12M 3/00* (2006.01)

(52) U.S. Cl.
CPC ......... *G01N 33/4836* (2013.01); *C12M 21/08* (2013.01); *C12M 35/02* (2013.01); *C12M 41/46* (2013.01)

(58) Field of Classification Search
None
See application file for complete search history.

(56) References Cited

PUBLICATIONS

Chuang et al. "Multifunctional microelectrode array (mMEA) chipforneural-electrical and neural-chemical interfaces: Characterization of comb interdigitated electrode towards dopamine detection." BiosensorsandBioelectronics41(2013)602-607. (Year: 2013).*

(Continued)

*Primary Examiner* — William H. Beisner
(74) *Attorney, Agent, or Firm* — Zilka-Kotab, P.C.

(57) ABSTRACT

A method includes simultaneously measuring electrophysiological responses and contractility responses of a plurality of cells forming a tissue culture using a system comprising a sensor array configured to simultaneously measure the electrophysiological responses and the contractility responses of the plurality of cells forming the tissue culture. Fabrication techniques for making such systems include: forming a sensor array comprising an interpenetrating arrangement of IDEs and electrodes of a MEA in or on a substrate surface; forming a plurality of contacts for interfacing the system with one or more external devices in or on the substrate surface; and forming leads between the plurality of contacts and the sensor array.

18 Claims, 12 Drawing Sheets

(56) References Cited

PUBLICATIONS

Enright et al. "Long-term non-invasive interrogation of human dorsal root ganglion neuronal cultures on an integrated microfluidic multielectrode array platform." Analyst, 2016, 141, 5346. (Year: 2016).*
Guo et al. "A PDMS-Based Integrated Stretchable Microelectrode Array (isMEA) for Neural and Muscular Surface Interfacing." IEEE Transactions on Biomedical Circuits and Systems, vol. 7, No. 1, Feb. 2013. (Year: 2013).*
Maccione et al. "Sensing and Actuating Electrophysiological Activity on Brain Tissue and Neuronal Cultures With a High-Density CMOS-MEA." Transducers 2013, Barcelona, Spain, Jun. 16-20, 2013. (Year: 2013).*
Wesche et al. "A nanoporous alumina microelectrode array for functional cell-chip coupling." Nanotechnology 23 (2012) 495303 (8pp). (Year: 2012).*
Xiao et al. "Evaluation of doxorubicin toxicity on cardiomyocytes using a dual functional extracellular biochip." Biosensors and Bioelectronics 26 (2010) 1493-1499. (Year: 2010).*
Chuang et al. "Multifunctional microelectrode array (mMEA) chip for neural-electrical and neural-chemical interfaces: Characterization of comb interdigitated electrode towards dopamine detection." Biosensors and Bioelectronics 41 (2013) 602-607 (with 17 pages of Supplement Mat. referenced on p. 603). (Year: 2013).*
Y. Sagi, P. J. Basser and Y. Assaf, "Estimation of Cell Size Using the Composite Hindered and Restricted Model of Diffusion" Proc. Intl. Soc. Mag. Reson. Med. 17 (2009) p. 1390.

* cited by examiner

SENSOR ARRAY AND APPARATUS FOR SIMULTANEOUS OBSERVATION OF TISSUE ELECTROPHYSIOLOGY, CONTRACTILITY, AND GROWTH

RELATED APPLICATIONS

The present application is a divisional of U.S. patent application Ser. No. 15/901,766, filed Feb. 21, 2018 (published Aug. 30, 2018 as U.S. Patent Publication No. US 2018/0246076 A1) and entitled "Sensor Array and Apparatus For Simultaneous Observation of Tissue Electrophysiology, Contractility, And Growth," which is entitled to the benefit of priority from U.S. Provisional Patent Application No. 62/463,534, filed Feb. 24, 2017. The present application hereby claims priority to, and incorporates by reference, U.S. patent application Ser. No. 15/901,766 and U.S. Provisional Patent Application No. 62/463,534.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to monitoring physiological conditions of tissue cultures, and more particularly to simultaneously measuring electrophysiological, tissue contractility, and/or growth characteristics of tissue cultures in real-time.

BACKGROUND

Tissue culture and observation is a critical component of many basic and translational research efforts, including evaluation of drug candidates and drug discovery. In order to facilitate new drug discovery, and evaluate suitability of candidate drugs, it is critical to determine the cardiological impact of such drugs on the patient. In particular, cardiac toxicity is a major cause of drug candidate failure and is responsible for retraction of many drug candidates. Often such toxicity is discovered late in the development and approval process, e.g. during non-human primate or clinical trials, after significant investment and research efforts have been expended.

Accordingly, it would be useful to provide technologies capable of evaluating cardiological impact of various substances, particularly drug candidates and cardiac toxicity thereof, to accelerate the drug discovery and approval process, while also reducing the effort and monetary resources associated with developing potentially toxic drugs to the point where conventional techniques, e.g. animal/clinical trials, can identify the risks associated therewith. Even more advantageous would be the development of such technologies which may evaluate cardiological impact in a high-throughput manner, e.g. utilizing existing high-throughput tissue culture equipment and instrumentation such as 96-well plates and associated instruments.

Conventional efforts to this effect include platforms capable of evaluating either electrophysiological response, contractility (i.e. mechanical response), or morphology/growth characteristics, under controlled conditions and in response to exposure to drug candidates.

In this vein, prevailing commercialized cardiac tissue platforms fall into two main categories: multi-electrode arrays (MEAs) for mapping extracellular action potentials, and interdigitated electrodes (IDEs) for measuring beating and viability. Both of these conventional systems have been integrated with multi-well plates to provide a high-throughput manner for assessing cardiotoxicity under different conditions.

However, each category is uniquely optimized to measure either electrophysiology or contractility, but not both. The MEA systems are designed to achieve high sensitivity in detecting local action potentials with high spatial resolution, but cannot provide information on tissue contractility. In contrast, the commercially available contractility measurement systems focus on measuring cell contractions by maximizing the conversion of mechanical movement of the tissue to electrical signals. This method requires the use of large-area opaque metal electrodes that cover the majority of the plate surface, limiting visualization of cell morphology. In addition, these conventional contractility measurement systems lack the ability to detect location-specific action potentials, depriving the observer of insight into how the tissue reacts to particular conditions (e.g. drug exposure) at fine resolution (e.g. cell-scale), and while capable of detecting motion, are incapable of quantifying the amount of force associated with contractions.

Hayakawa et al. (Image-based evaluation of contraction-relaxation kinetics of human-induced pluripotent stem cell-derived cardiomyocytes: Correlation and complementarity with extracellular electrophysiology." *J. Mol. Cell. Cardiol.*, 2014, 77, 178, hereafter "Hayakawa") reported imaged-based evaluation of contraction-relaxation kinetics of human induced pluripotent stem cell-derived cardiomyocytes (hiPS-CMs) cultured on a commercialized 64-channel MEA well plate. This work represents the first simultaneous measurement of motion and field potential (FP) in hiPS-CMs. The MEA plate was coated with hydrogels containing fluorescence microbeads as the motion tracker. Using a high-speed video acquisition with motion vector analysis to trace the contractile characteristics of cardiomyocytes (CMs), the authors studied the quantitative correlation between the FP and the contractile motion of hiPSCMs in the presence of various drugs.

Maddah et al. ("A non-invasive platform for functional characterization of stem-cell-derived cardiomyocytes with applications in cardiotoxicity testing." *Stem Cell Rep.*, 2015, 4, 621, hereafter "Maddah") also used video acquisition and subsequent image-analysis algorithms to resolve beating behavior coupled with simultaneous patch clamp recording, and demonstrated good correlation between the two data traces.

In addition, ongoing efforts to integrate one-dimensional nanowires or pillar geometries with planar electrodes in microfluidic channels and mesh platforms show promise for new insight into cardiac function.

However, the foregoing conventional designs of contraction detection using only electrophysiological measurement, contractility measurement, morphology measurement, and/or relying on image-base analysis are adverse to data collection in a high-throughput manner.

Accordingly, it would be useful to provide technologies which may evaluate impact of various conditions, particularly drug exposure, on tissue systems in a high-throughput manner from multiple perspectives, including at least electrophysiological and contractility measurements, and preferably also morphology and/or other growth-based measurements, simultaneously and in real time.

SUMMARY

According to one embodiment, a method includes: simultaneously measuring electrophysiological responses and contractility responses of a plurality of cells forming a tissue culture using a system including a sensor array configured to simultaneously measure the electrophysiological responses and the contractility responses of the plurality of cells forming the tissue culture.

According to yet another embodiment, a method of forming a system for simultaneously measuring electrophysiological responses and contractility responses of a tissue includes: forming a sensor array comprising an interpenetrating arrangement of interdigitized electrodes (IDEs) and electrodes of a multi-electrode array (MEA) in or on a substrate surface; forming a plurality of contacts for interfacing the system with one or more external devices in or on the substrate surface; and forming leads between the plurality of contacts and the sensor array.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

As referred to herein, "interpenetrating" structures such as electrodes, arrays, etc. are to be understood as characterized by an interleaving or alternating pattern in which elements of each respective component of the "interleaving" structure are present throughout substantially all of the structure as a whole. For example, in various embodiments "interpenetrating" structures may include interleaved "finger" arrangements, concentric shapes, coinciding serpentine, spiral, etc. patterns of lines, grids, etc. with the sole requirement that portions of each respective component of the overall structure are distributed throughout a shared plane defining the structure.

Figure 3A:
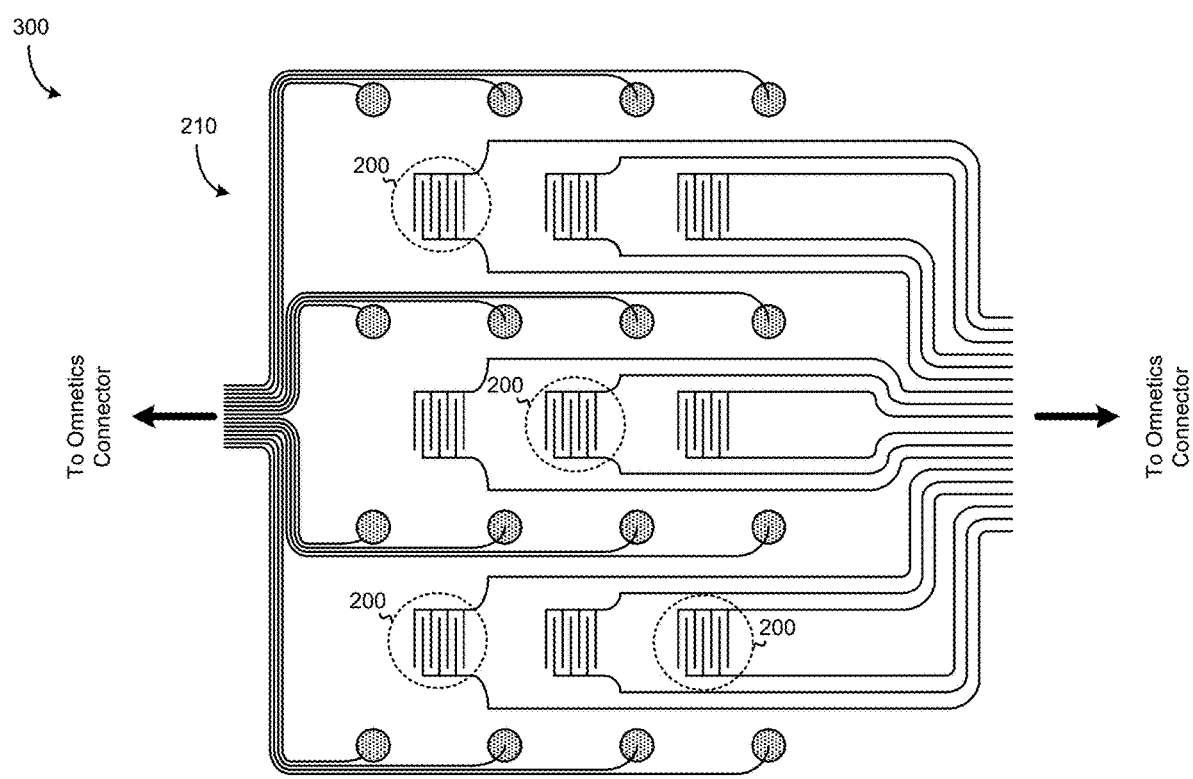
FIG. 3A is a simplified schematic of a sensor array including interpenetrating MEA and IDE elements, according to one embodiment.
Figure 3B:
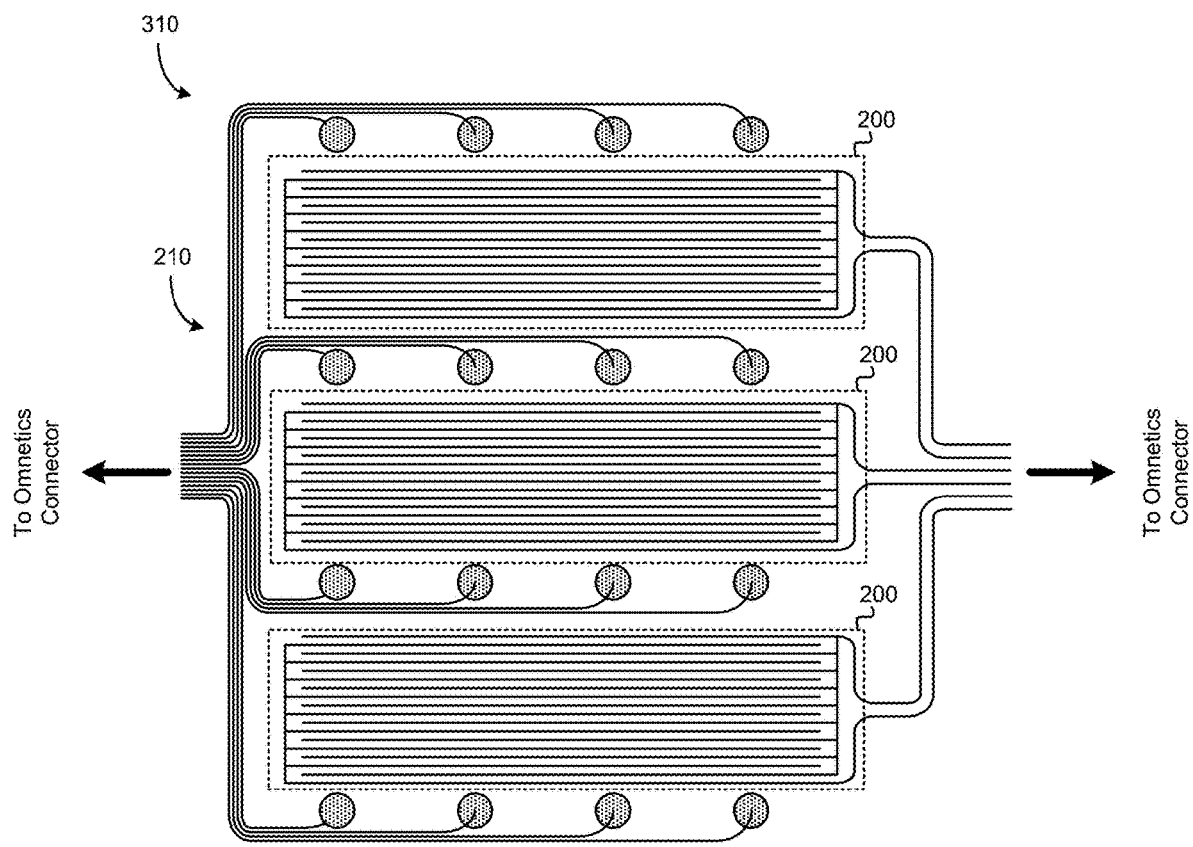
FIG. 3B is a simplified schematic of a sensor array including interpenetrating MEA and IDE elements, according to one embodiment.
Figure 3C:
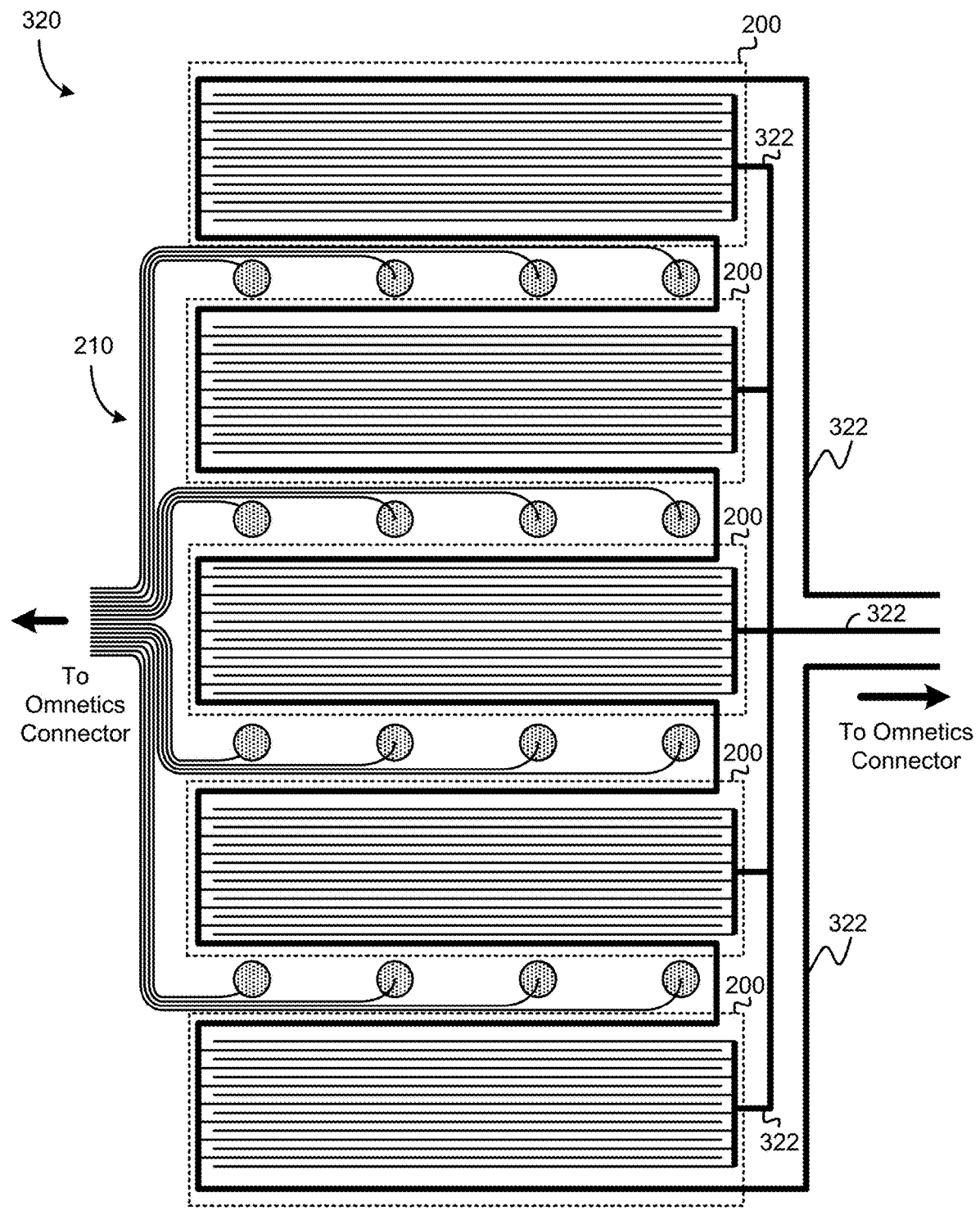
FIG. 3C is a simplified schematic of a sensor array including interpenetrating MEA and IDE elements, according to one embodiment.

In preferred approaches, "interpenetrating" structures include interleaved protrusions of each respective component of the structure extending from opposing sides of the shared plane, and most preferably include interleaved protrusions of MEAs and IDEs in an alternating fashion, such as shown in FIGS. 3A-3C, according to several exemplary embodiments.

The following description discloses several preferred embodiments of systems and methods for tissue culture and observation, and more particularly, this invention relates to sensor arrays and tissue culture apparatuses incorporating such sensor arrays, as well as related methods of making and using such materials. The sensor arrays are suitable for simultaneously measuring electrophysiological characteristics/responses and contractility characteristics/responses of tissue systems placed in proximity therewith, e.g. in a tissue culture apparatus incorporating such sensor arrays. The tissue culture system also advantageously allows simultaneous measurement of tissue growth characteristics in real-time or near real-time along with measurement of the electrophysiological and/or contractility characteristics/responses.

The presently disclosed inventive concepts include a novel platform design that can noninvasively measure the tissue growth, electrophysiology and contraction simultaneously in real time. By adopting a novel design consisting of interpenetrating multi-electrode array (MEA) and interdigitized electrode (IDE) geometries, the platform is capable of electrical stimulation, field potential (FP) mapping, contraction recording and optical observation of cardiac cells and tissues.

As a proof of principle, and in accordance with one exemplary embodiment described in further detail below, human induced pluripotent stem cell-derived cardiomyocytes (iPS-CMs) were cultured on the system and the platform was further validated with blebbistatin, an excitation-contraction decoupler. In addition, the effect of the drug norepinephrine was investigated using this platform and its mechanism was elucidated by computational results.

According to one general embodiment, a sensor array for simultaneously measuring electrophysiological responses and contractility responses of a tissue includes: a substrate; a multi-electrode array (MEA) disposed in or on the substrate; and a plurality of interdigitized electrodes (IDEs) disposed in or on the substrate. The MEA and the IDEs are interpenetrating within a plane substantially parallel to an upper surface of the substrate.

As used throughout this disclosure and in the appended claims, the phrase "in or on" is intended to encompass embodiments such as those where one component is physically in the other component, e.g., embedded therein, integrally formed therein, etc.; one component is on the other component, e.g., formed thereon in any manner, coupled thereto, etc.; and combinations of in and on, e.g., where one component is partially in and partially on the other component.

According to another general embodiment, a method includes: simultaneously measuring electrophysiological responses and contractility responses of a plurality of cells forming a tissue culture using a system. The system includes: a sensor array for simultaneously measuring electrophysiological responses and contractility responses of a tissue. The sensor array includes: a substrate; a multi-electrode array (MEA) disposed in or on the substrate; and a plurality of interdigitized electrodes (IDEs) disposed in or on the substrate. The MEA and the IDEs are interpenetrating within a plane substantially parallel to an upper surface of the substrate. The system also includes a first set of Omnetics connectors disposed in or on a surface of the substrate along one side of the substrate and electrically coupled to the sensor array via a plurality of MEA leads; a second set of Omnetics connectors disposed in or on a surface of the substrate along an opposing side of the substrate as the first set of Omnetics connectors and electrically coupled to the sensor array via a plurality of IDE leads; a cell culture chamber; and an enclosure surrounding the sensor array, the first and second sets of Omnetics connectors, and the cell culture chamber.

According to yet another general embodiment, a method of forming a system for simultaneously measuring electrophysiological responses and contractility responses of a tissue includes: forming a sensor array comprising an interpenetrating arrangement of interdigitized electrodes (IDEs) and electrodes of a multi-electrode array (MEA) in or on a substrate surface; forming a plurality of contacts for interfacing the system with one or more external devices in or on the substrate surface; and forming leads between the plurality of contacts and the sensor array.

In general, the "lab-on-a-chip" device disclosed herein includes a glass substrate with patterned microelectrodes, two sets of Omnetics connectors, and a cylindrical cell culture chamber. The patterned microelectrodes, in various embodiments, include an MEA (e.g. including 16 electrodes), a modified IDE geometry (e.g. including 3-9 IDE units), a ground electrode and a pair of stimulation electrodes (See FIG. 5A). Each set of microelectrodes is preferably connected to separate Omnetics connectors or any equivalent thereof that would be appreciated by a skilled artisan reading the present descriptions, for interfacing with separate instrumentation (e.g. as shown in FIG. 1).

Figure 1:
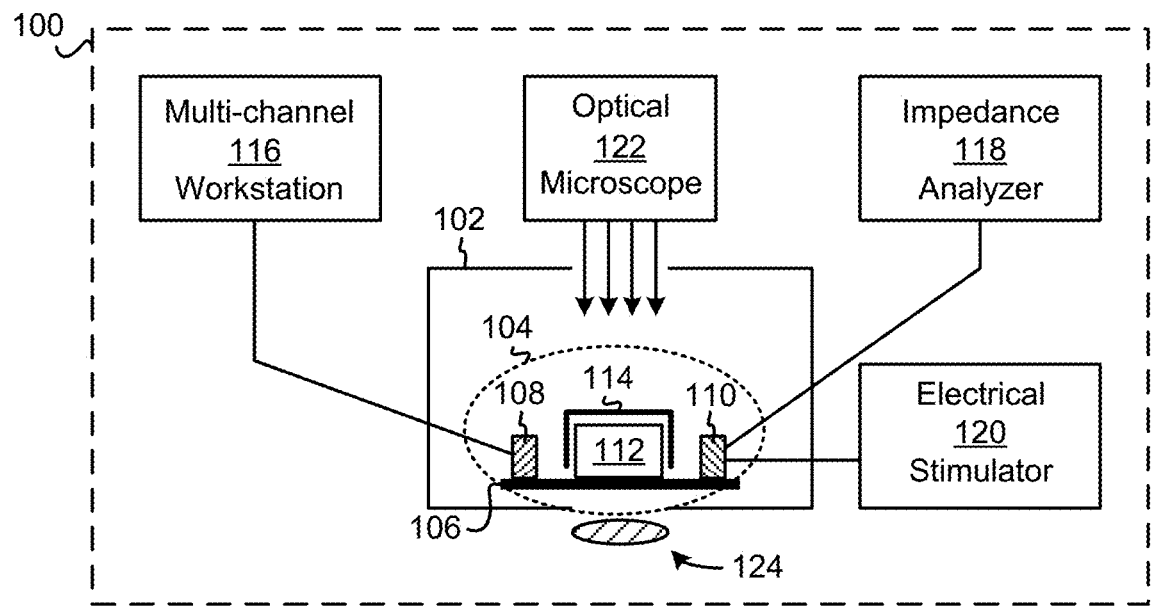
FIG. 1 is a simplified schematic of a system for simultaneously measuring electrophysiological responses and contractility responses of a tissue, according to one embodiment.

More specifically, and again with reference to the exemplary embodiment of FIG. 1, a system 100 for simultaneously measuring electrophysiological responses and contractility responses of a tissue includes an enclosure 102 having disposed therein a "lab-on-a-chip" 104 electrically and/or communicatively coupled to a plurality of additional instrumentation, in preferred approaches. The lab-on-a-chip 104 includes a substrate 106 having disposed therein/thereon a sensor array (not shown in FIG. 1) such as depicted in FIGS. 2A-4B and described in further detail below, in various approaches.

The lab-on-a-chip 104 also includes a first set of Omnetics connectors 108 and second set of Omnetics connectors 110 disposed in/on the substrate and configured to provide electrical and/or communicative coupling to the additional instrumentation. Additional instrumentation may include, for example, a multichannel workstation 116 electrically and/or communicatively coupled to the first set of Omnetics connectors 108 and an impedance analyzer 118 and electrical stimulator 120 electrically and/or communicatively coupled to the second set of Omnetics connectors 110.

Critically, the lab-on-a-chip 104 also includes a tissue culture chamber 112, which may be sealed from exposure to the rest of the enclosure 102 via a lid 114. Tissue culture chamber 112 is positioned in proximity to, and preferably directly above or in contact with, the sensor array so as to facilitate simultaneous measurement of the electrophysiological and contractility characteristics of tissue growing in the tissue culture chamber 112. Accordingly, in one embodiment the tissue culture chamber 112 is positioned between the first set of Omnetics connectors 108 and second set of Omnetics connectors 110.

Moreover, and with continuing reference to FIG. 1, the lab-on-a-chip 104 may be operatively coupled to an optical microscope 122 and objective lens 124, such operative coupling including suitably located apertures (e.g. windows, preferably sealed by optically transparent material so as to prevent exposure of the enclosure 102 environment to external contaminants, etc.) in the enclosure 102 and positioning of the optical microscope 122 and objective lens 124 so as to define a path therebetween which includes the tissue culture chamber 112. Accordingly, in preferred approaches the lid 114 is also optically transparent.

Optical Measurements

The foregoing configuration advantageously allows facile optical inspection of tissue cultures growing in the tissue culture chamber 112, thereby enabling the optical observation of cell morphology and growth characteristics, in conjunction with the novel configuration of the sensor array so as to allow sufficient absorption, transmittance, etc. of light from the optical microscope 122 to the objective lens 124 to permit such morphological observations. For instance, in various embodiments the spacing between elements of the sensor array (e.g. electrodes of the MEA and IDEs) has a magnitude of at least the mean diameter of individual cells of the tissue system to be interrogated. In one exemplary embodiment involving optical observation of CMs, a spacing between the elements of the sensor array in an amount of at least 50 microns, more preferably 100 microns or more, was enforced so as to permit optical investigation of individual CM cells having an average diameter of approximately 20-50 microns.

Contractility Measurements

The underlying mechanism of monitoring tissue growth and contraction using IDEs originates from the fact that the tissue layer functions as an insulator, and its behavior can be described as a R//C parallel circuit in a simplified equivalent circuit model. As cells grow and cover the IDE, the current flow between the working and counter electrodes is impeded in direct correlation to: the number of cells covering the electrode, the cell morphology, and the nature of the cell adherence. These factors lead to changes in the impedance readout. Furthermore, when cells contract, the gaps between the cells and the gap between the cell layer and substrate are altered on the (sub)nanometer scale, leading to small changes in both R and C, which can be detected as change in bioimpedance (Δ|Z|bio) by a sensitive IDE at an optimal frequency.

Accordingly, contraction may be measured by recording the change in bioimpedance associated with the tissue morphology change that occurs during cell beating. In the case of a tissue-covered electrode, the apparent total impedance recorded by an IDE includes contributions from solution resistance (|Z|solution), electrode capacitance and resistance (|Z|electrode), and the bioimpedance (|Z|bio) from the tissue, which can be described in a classic Randle circuit model. Because the change in bioimpedance due to cardiac contraction is very small, the IDE must be designed to minimize the non-biological contribution of |Z|.

In general, an IDE can be characterized by its cell constant, K, which is a geometry-dependent parameter that relates the electrochemical cell conductance ($R_s$) to the solution's conductivity (σ) through Rs=K/σ, and electrochemical cell capacitance ($C_e$) to the solution's dielectric constant (ε) through $C_e$=ε/K. Note that lower K values are desired to achieve reduced |Z|solution and |Z|electrode, therefore providing guidance for IDE design.

Accordingly, for basic IDE geometries, the cell constant can be calculated from IDE geometry according to the following equation (where L is the overlay finger length, W is the finger width, S is the space between adjacent fingers, and N is the total number of fingers in the IDE).

$$K=2\{[\sqrt[3]{(S/W)}]/L(N-1)\} \quad \text{(Eqn. 1)}$$

For IDE structures composed of several IDE cells (n) connected in parallel, the cell constant K diminishes n times compared to that of the unit cell (K/n).

Figure 2A:
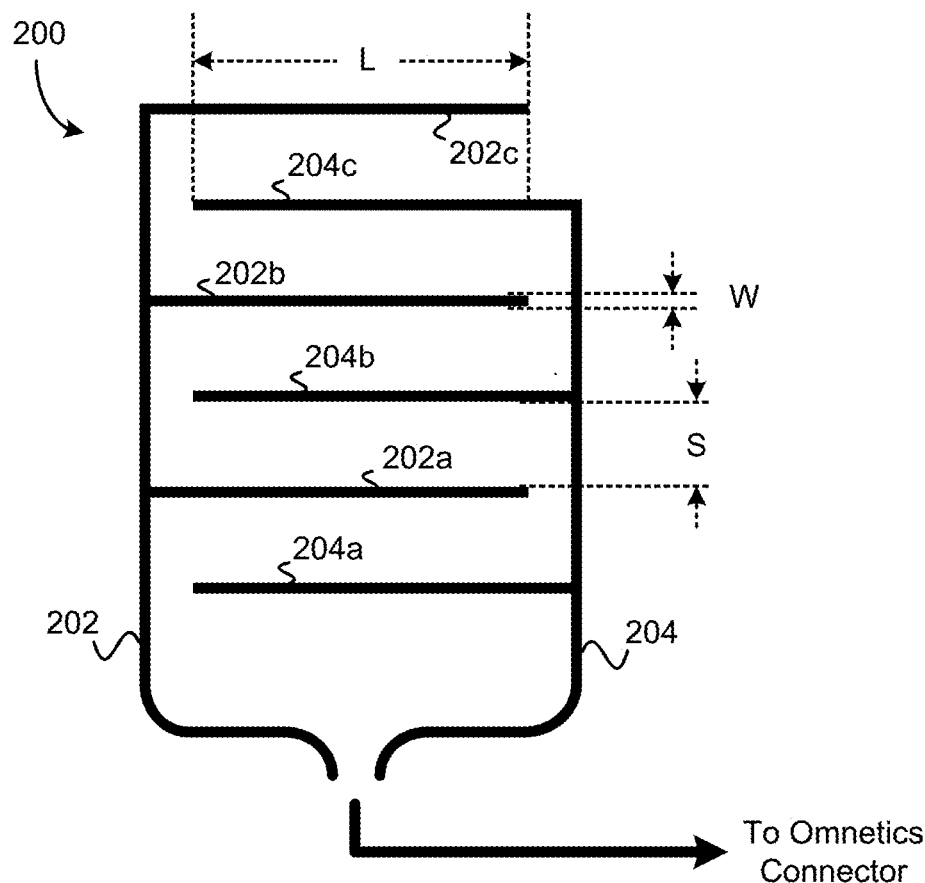
FIG. 2A is a simplified schematic of an interdigitized electrode (IDE) structure, according to one embodiment.

Turning now to FIG. 2A, a simplified schematic of an interdigitized electrode (IDE) 200 structure and the spatial characteristics thereof referenced above in equation 1 is shown, according to one embodiment. The IDE 200 includes first and second leads 202, 204, and interdigitized fingers 202a-202c and 204a-204c. The leads and interdigitized fingers preferably comprise thin films of gold, platinum, platinum black, titanium, carbon nanotubes, or any combination thereof. FIG. 2A represents a general configuration advantageous for IDEs 200 and the use thereof to measure contraction and/or contractility characteristics of tissue systems, in the context of the presently disclosed inventive concepts.

To determine an optimal IDE geometry for measuring tissue contraction, the context of the presently disclosed inventive concepts include four preferred IDE geometries (shown and described in further detail below with reference to FIGS. 3A-4B). Geometry A (FIG. 3A) & B (FIG. 3B) are individual IDE arrays, while geometry C & D (FIG. 3C) are serially connected IDE assemblies. Geometries E & F (FIGS. 4A-4B) depict fractal IDE geometries which may be used in combination with, or instead of, the IDE geometries shown in FIGS. 3A-3C, in various embodiments. Each of the IDE arrays/assemblies shown in FIGS. 3A-4B is combined with a MEA and arranged in an interpenetrating configuration to form the sensor arrays of the presently disclosed inventive concepts. In various embodiments, sensor arrays may include any combination of the geometries for individual electrodes, IDE arrays, etc. and/or any combination of the interpenetrating arrangements as shown in FIGS. 3A-4B, without departing from the scope of the instant descriptions.

Electrophysiological Measurements

Complementing the contraction measurement, the MEA of the sensor array provides information on the electrical propagation within the same (resting or contracting) tissue measured by the IDE.

Figure 6A:
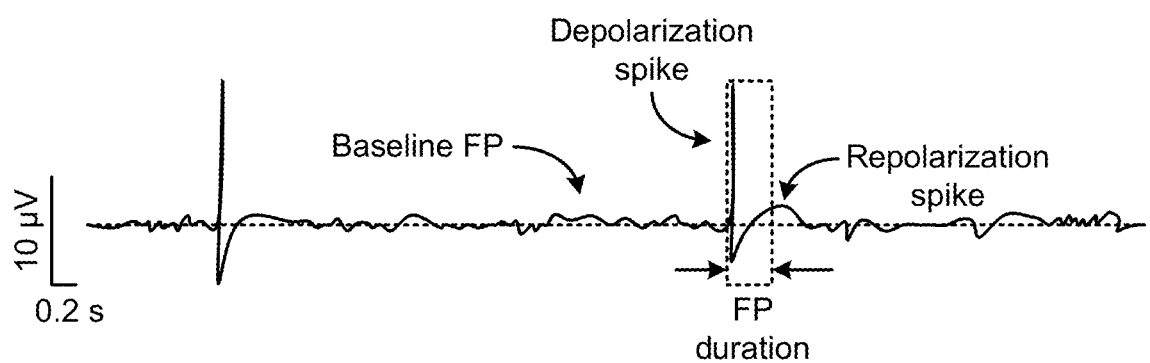
FIGS. 6A-6C depict experimental results of observing electrophysiological responses including field potential changes within a tissue culture, according to one embodiment.

Within a single peak, it is advantageously possible to resolve a typical cardiac FP profile that consists of a depolarization spike (e.g. about 5 ms in duration, 4.3 ms in one experiment) followed by a FP duration (e.g. about 250-300 ms, and about 260 ms in one experiment), and a repolarization spike to the baseline, with a repeating cycle length of approximately 10 seconds (e.g. 9.4 seconds in one experiment), as shown in accordance with one embodiment in FIG. 6A.

Figure 6B:
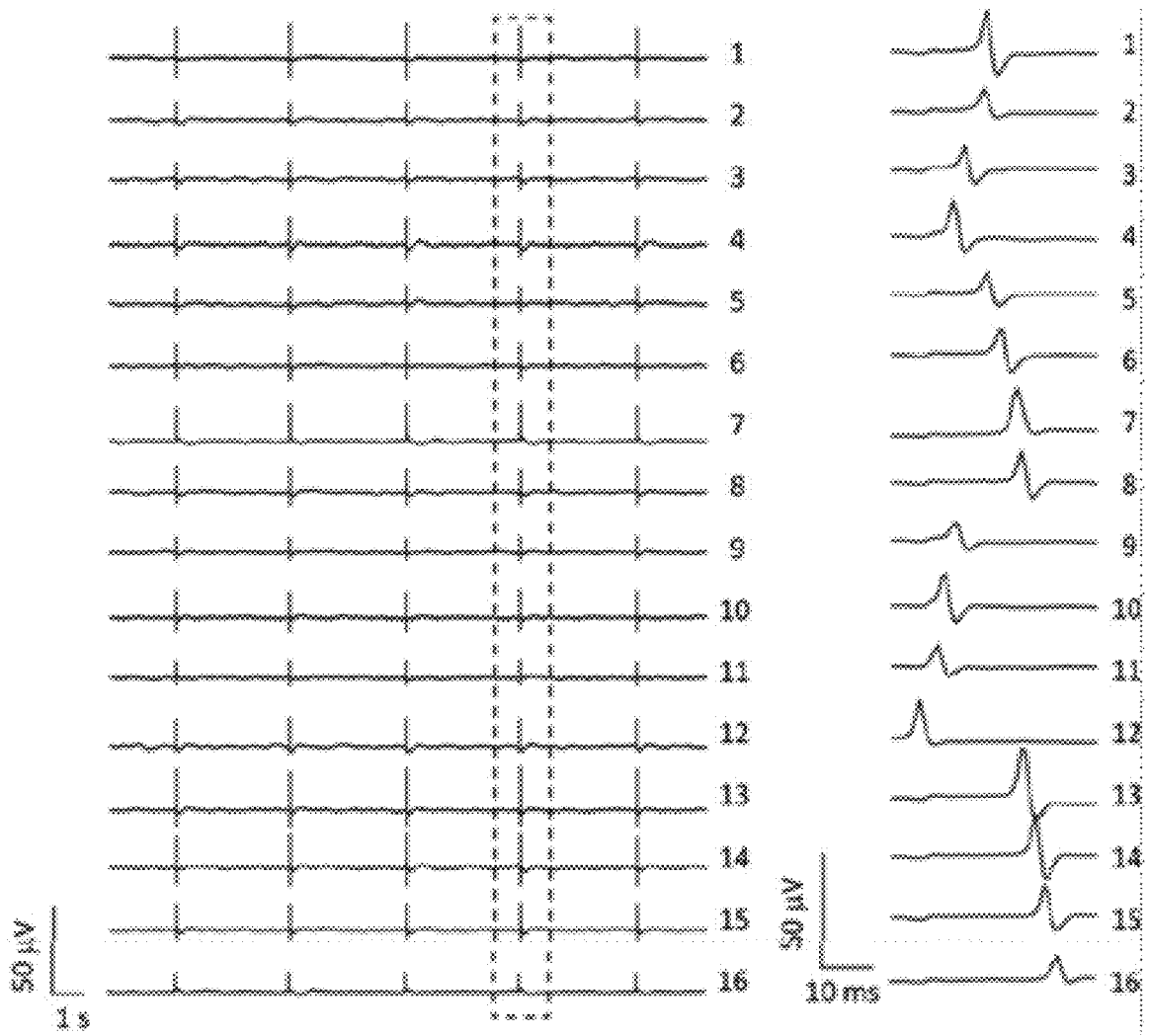

FIG. 6B shows extracellular field potentials (FPs) recorded simultaneously from a MEA of a sensor array positioned under a tissue culture incubated for two days in-vitro in a system such as shown and discussed above with reference to FIG. 1. In accordance with the contraction behavior evidenced by optical observation and impedance recording, rhythmic peaks may be observed within all the MEA channels, with amplitudes ranging from 9 to 35 μV in one experiment.

In addition, temporal comparison of peaks reveals each electrode is capable of sensing the arrival of the FP with a well-defined temporal offset, based on which an activation map was generated for direct visualization of the impulse initiation and conduction across the 2D tissue during a spontaneous contraction.

Figure 6C:
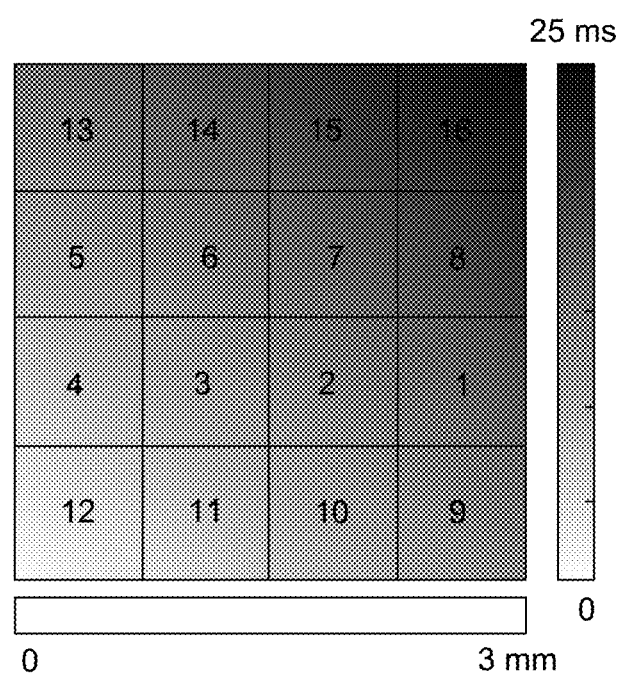

A representative map is shown in FIG. 6C, according to one embodiment. In this case, within the 3 mm by 3 mm area defined by the MEA, electrical activation was initiated from the bottom left electrode in the MEA, and then propagated upwards through the rest of the tissue. In this experimental embodiment, the calculated global conduction velocity was 16.0 cm/s, comparable with reported values of 3.5 to 20.1 cm/s for in vitro cultured immature hiPSCM monolayers, suggesting good intercellular electrical coupling of the tissues grown in the system.

Figure 2B:
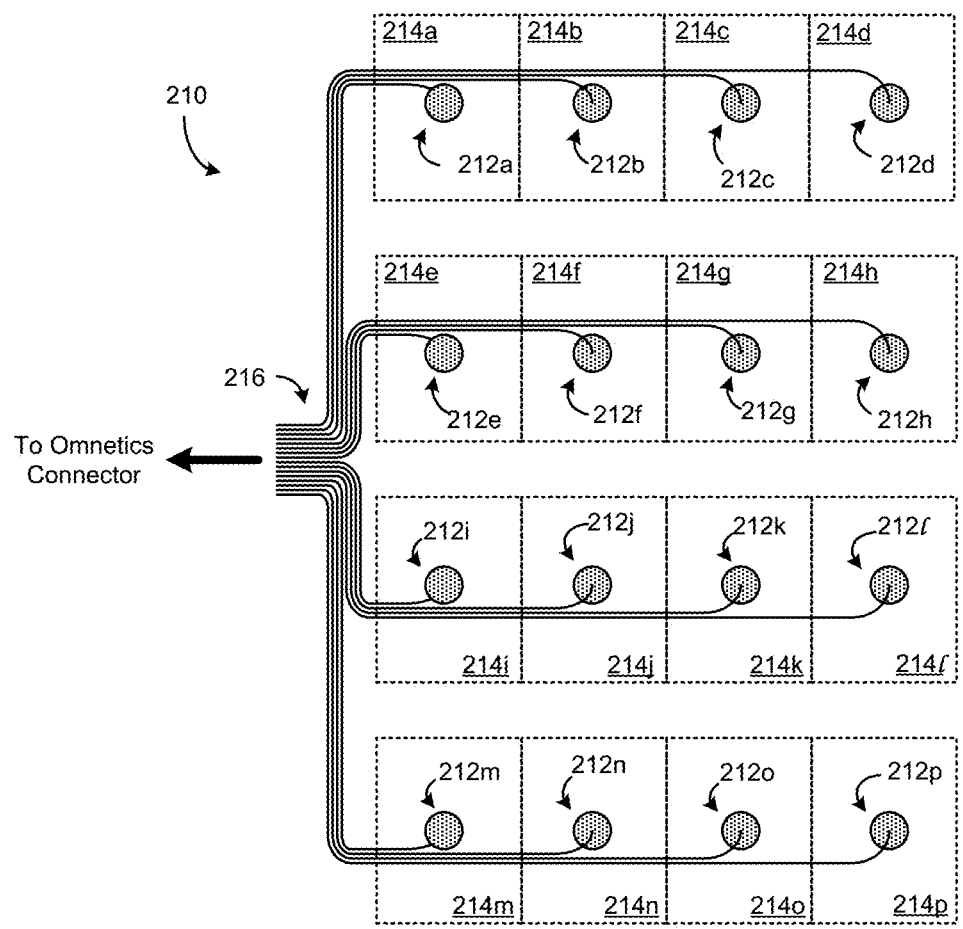
FIG. 2B is an exemplary simplified schematic of a multi-electrode array configuration, according to one embodiment.

Accordingly, and turning now to FIG. 2B, an exemplary multi-electrode array (MEA) 210 configuration is shown, according to one embodiment. The MEA 210 as shown in FIG. 2B includes 16 electrodes 212a-212p arranged in a coplanar, substantially rectangular grid including discrete detection zones 214a-214p. Although the detection zones 214a-214p as shown in FIG. 2B do not entirely encompass the area of the MEA, in preferred embodiments zones 214a-214p (or the equivalent number thereof) form a substantially complete area of detection within the boundaries of the sensor array in which the MEA 210 is included. Similarly, detection zones 214a-214p may have different shapes than those shown in FIG. 2B, e.g. circular, ovular, etc. as would be appreciated by a person having ordinary skill in the art upon reading the present descriptions.

Although there are 16 electrodes 212a-212p arranged in a coplanar grid according to the embodiment of FIG. 2B, skilled artisans will appreciate that other arrangements, e.g. circular, ovular, square, hexagonal, or any other polygonal arrangement of electrodes 212a-212p may be employed without departing from the scope of the presently disclosed inventive concepts. Similarly, other numbers of electrodes 212a-212p may be implemented without departing from the scope of the inventive concepts presented herein. The sole restriction on such arrangements is that the electrodes 212a-212p are preferably arranged in a substantially coplanar arrangement, and preferably the plane of the electrodes 212a-212p is parallel to the plane of the upper surface of the substrate into/onto which the electrodes are disposed.

Figure 5A:
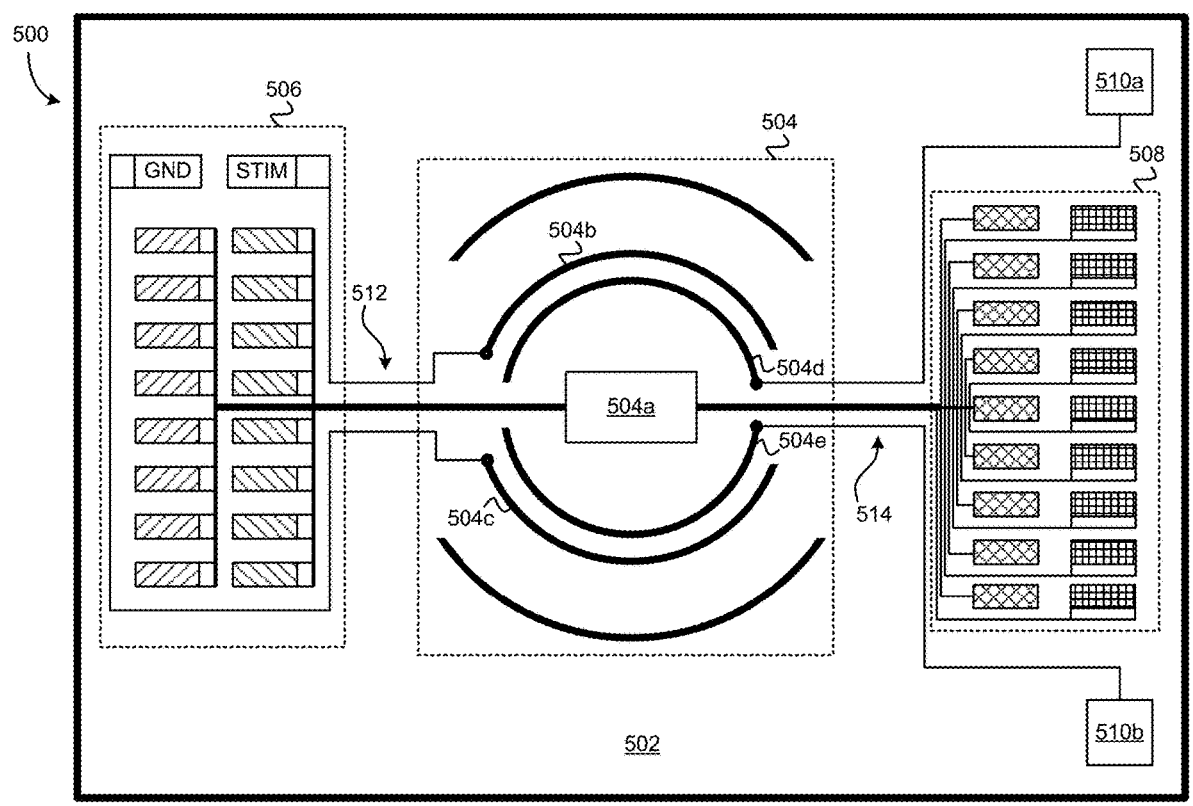
FIG. 5A is a simplified schematic of a lab-on-a-chip system for simultaneously measuring electrophysiological responses and contractility responses of a tissue, according to one embodiment.

Each of the electrodes 212a-212p is electrically coupled to a lead 216 leading to a contact of an Omnetics connector (not shown in FIG. 2B, but see FIG. 5A).

The exemplary IDE 200 structure and MEA 210 structure shown in FIGS. 2A-2B may be employed in various combinations and modifications thereof to form a sensor array suitable for simultaneous measurement of electrophysiological, contractility, and/or morphological/growth characteristics and responses, in various embodiments of the presently disclosed inventive concepts and, for example, as shown in FIGS. 3A-3C.

Figure 7A:
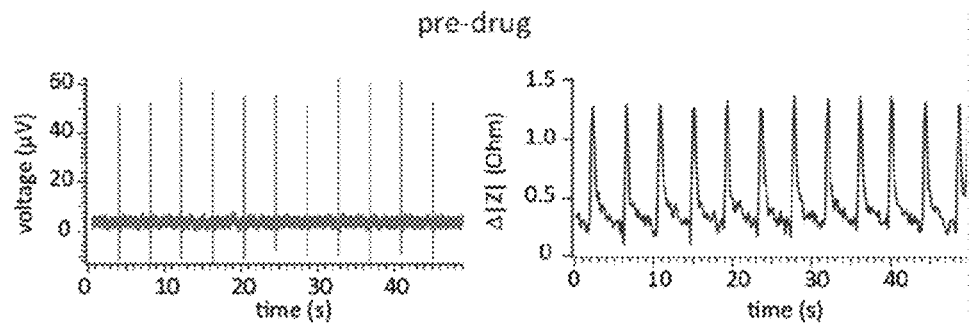
FIGS. 7A-7C depict experimental results demonstrating simultaneous measurement of electrophysiological responses and contractility responses within a tissue culture, according to one embodiment.
Figure 7B:
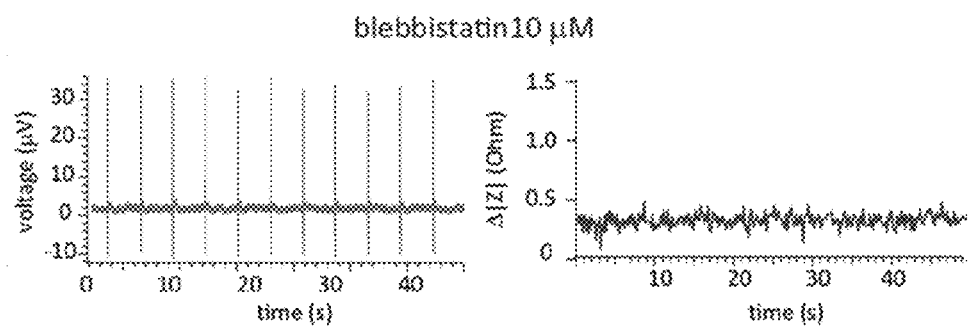
Figure 7C:
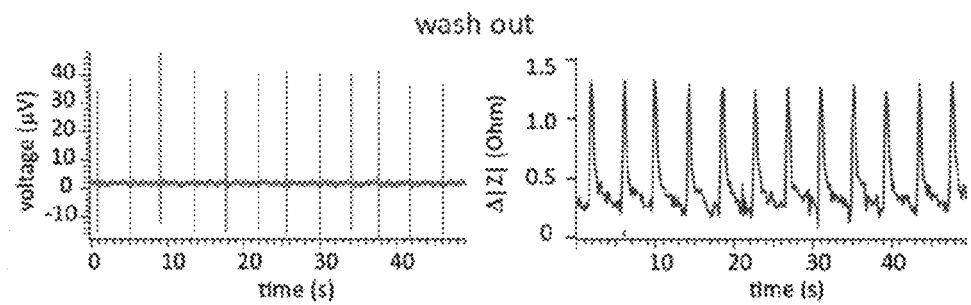

As proof of principle of the inventive sensor arrays' capability to simultaneously detect electrophysiological responses (field potentials) and contractility (mechanical responses via impedance changes), the inventors conducted measurements as described above on a CM tissue culture pre- and post-exposure to blebbistatin, which blocks contraction but does not interfere with field potential generation of CM tissues. Measurements were repeated once more after washing the culture to flush the blebbistatin from the system. FIGS. 7A-7C show the field potential (left) and corresponding impedance changes (right) prior to exposure to blebbistatin (FIG. 7A), after exposure to blebbistatin (FIG. 7B) and following flushing of blebbistatin from the system (FIG. 7C).

Prior to compound addition, the tissue beat spontaneously and rhythmically at a rate of 14 bpm, as shown from both the FP profile and impedance profile of FIG. 7A. After incubation with 10 μM blebbistatin, the tissue was observed to be static under an optical microscope, and the impedance recording showed a flat baseline signal, while the MEA data showed the action potential pattern was not affected (FIG. 7B). Washing out of the chemical restored the tissue contractility, as reflected by the rhythmic impedance peaks as well as under optical observation (FIG. 7C). These data unambiguously demonstrate the cardiac platform's capability to provide real-time information of tissue electrophysiology and contraction signals with good correlation and reliability.

Turning now to exemplary structures and geometries of interpenetrating MEA and IDE elements of a sensor array in accordance with the presently disclosed inventive concepts, several nonlimiting but illustrative embodiments are shown in FIGS. 3A-4B.

With reference to FIG. 3A, an exemplary sensor array 300 is shown, according to one embodiment. The array 300 includes a plurality of IDEs 200 and a MEA 210 as shown in FIGS. 2A-2B, in accordance with one potential embodiment thereof. In particular, sensor array 300 as shown in FIG. 3A includes nine IDEs 200 arranged in three rows, or finger-like protrusions, each row including three IDEs 200. The nine IDEs 200 are arranged in a substantially rectangular grid arrangement, and preferably are located in regions of the sensor array 300 between other of the IDEs 200 and the electrodes of the MEA 210. For instance, the electrodes of the MEA 210 and the IDEs 200 may form a substantially checkerboard pattern, with the electrodes of the MEA 210 and the IDEs corresponding to white or black positions (but not a mixture thereof), in one embodiment.

With continuing reference to FIG. 3A, each of the IDEs 200 may be electrically coupled to a pair of leads, which respectively are electrically coupled to contacts of an Omnetics connector, e.g. a second set of Omnetics connectors as described with reference to FIGS. 1 and 5A. Electrodes of the MEA 210 are similarly and preferably electrically coupled to contacts of a different, e.g. first, Omnetics connector as described above with reference to FIG. 2B. In accordance with the configuration of sensor array 300, each of the MEA electrodes 212a-212p and the IDEs 200 are individually connected to contact(s) of the Omnetics connector interface, as opposed to the serially connected IDEs of FIG. 3C, as described in further detail below.

In particularly preferred approaches, the sensor array 300 occupies a single plane, such that the electrodes of the MEA 210, IDEs 200, and associated leads are co-planar, and more preferably occupy a plane substantially parallel to a plane of an upper surface of a substrate into/onto which the sensor array 300 is disposed.

Although not drawn to scale, skilled artisans will appreciate that several primary advantages of a sensor array 300 such as shown in FIG. 3A include suitable spacing between electrodes and leads to permit optical inspection of tissue culture placed in proximity to (e.g. above) the sensor array 300, permitting that the substrate into/onto which the sensor array 300 is disposed and any other equipment such as an enclosure 102 and lid 114 as described above with reference to FIG. 1 also allows for such optical inspection. For instance, in one approach the spacing between elements of the sensor array such as electrodes, leads, and/or fingers of an IDE structure may be about 50 microns or more, preferably about 100 microns or more, in several embodiments. This advantageously allows simultaneous observation of morphological characteristics in conjunction with electrophysiological and/or contractility observations.

As noted above, one particular additional advantage that is conveyed by the use of a substantially grid-like arrangement of electrodes of the MEA 210 and the IDEs 200 (although to a lesser extent than for electrodes of the MEA 210) is the ability to map in two dimensions the propagation of field potential across a tissue culture by correlating observed field potential with location over time. A dispersed, regular arrangement of the electrodes of the MEA enables this functionality and represents an improvement in the art of tissue culture and tissue culture devices over the conventional platforms presently available.

For instance, in one embodiment using a sensor array 300 such as shown in FIG. 3A, the MEA 210 was connected via Omnetics connectors to an AlphaLab SnR multi-channel recording system (Alpha Omega, Alpharetta, GA) to record voltages as a function of time across all 16 electrodes of the MEA 210. Offline analysis of temporal differences between the 16 electrodes when voltage spikes occur generates an activation map such as shown in FIG. 6C. The activation map illustrates FP spatial propagation in the cardiac tissue monolayer across the surface area of the device.

Turning now to FIG. 3B, a second configuration, also referred to herein as "geometry B," of a sensor array 310 is shown, according to one embodiment. The MEA 210 of sensor array 310 is substantially identical to the MEA 210 of sensor array 300. However, instead of individual IDEs 200 being positioned between the vertical and horizontal position of the electrodes of the MEA as in sensor array 300 (e.g. in a checkerboard pattern), the IDEs 200 of sensor array 310 are individually connected via a pair of leads to a contact or contact(s) of the Omnetics connector interface.

Moreover, the IDEs 200 in accordance with sensor array 310 span substantially an entire region between adjacent sets of MEA electrodes, forming an interpenetrating arrangement of IDEs 200 and MEA electrodes 212a-212p.

FIG. 3C similarly shows a sensor array 320 comprising an interpenetrating arrangement of IDEs 200 and MEA electrodes 212a-212p, but in accordance with the embodiment of FIG. 3C the IDEs 200 are serially connected via IDE leads 322, which both connect the IDEs 200 to the contacts of the Omnetics connector interface and substantially surround the IDEs 200, interleaving between each finger-like protrusion of interpenetrating MEA 210 and IDEs 200 in a substantially serpentine fashion.

Both of geometries "C" and "D" as referred to herein conform to the general pattern of sensor array 320 as shown in FIG. 3C, but the scale of geometry "D" is approximately 5-fold greater than the scale of geometry "C" while maintaining all other spatial relationships between the individual elements of the sensor array 320, including relative MEA electrode position and/or spacing, relative IDE/MEA electrode position and/or spacing, relative lead spacing and/or position, number of leads, IDEs, and MEA electrodes, etc. as would be understood by a person having ordinary skill in the art upon reading the present descriptions.

For instance, in various exemplary embodiments, geometries A-C of sensor array 320 may be characterized by dimensions of approximately 1.5 mm by approximately 1.5 mm (length×width) and an overall area of approximately 2.25 mm$^2$ while geometry D of sensor array 320 may be characterized by dimensions of approximately 7.5 mm by 7.5 mm (length×width) an overall area of about 56.25 mm$^2$. As in sensor array 310, sensor array 320 includes IDEs 200 that span the entire region between finger-like protrusions of MEA 210. However, sensor array 320 includes five IDEs rather than three as in sensor array 310, with the IDEs. 200 being the external-most features of the sensor array rather than upper and lower sets of MEA electrodes 212a-212d and 212m-212p, respectively.

Table 1 below shows exemplary parameters of an illustrative embodiment of each of the geometries A-D. Skilled artisans should appreciate that aspects of the geometries may be modified and/or combined without departing from the scope of the presently disclosed inventive concepts.

TABLE 1

Geometry Parameters

| Geometry | # of IDE fingers | Finger Length (μm) | Overlay Length (L, μm) | Finger Width (W, μm) | Inter-space Distance (S, μm) | # of IDEs | Electrode Area (cm$^2$) |
|---|---|---|---|---|---|---|---|
| A | 10 | 100 | 88 | 5 | 5 | 9 | 5.00 × 10$^{-5}$ |
| B | 20 | 1000 | 990 | 5 | 5 | 3 | 1.00 × 10$^{-3}$ |
| C | 21 | 1400 | 1390 | 5 | 5 | 5 | 7.35 × 10$^{-3}$ |
| D | 31 | 4000 | 3806 | 10 | 10 | 5 | 6.20 × 10$^{-3}$ |

Figure 4A:
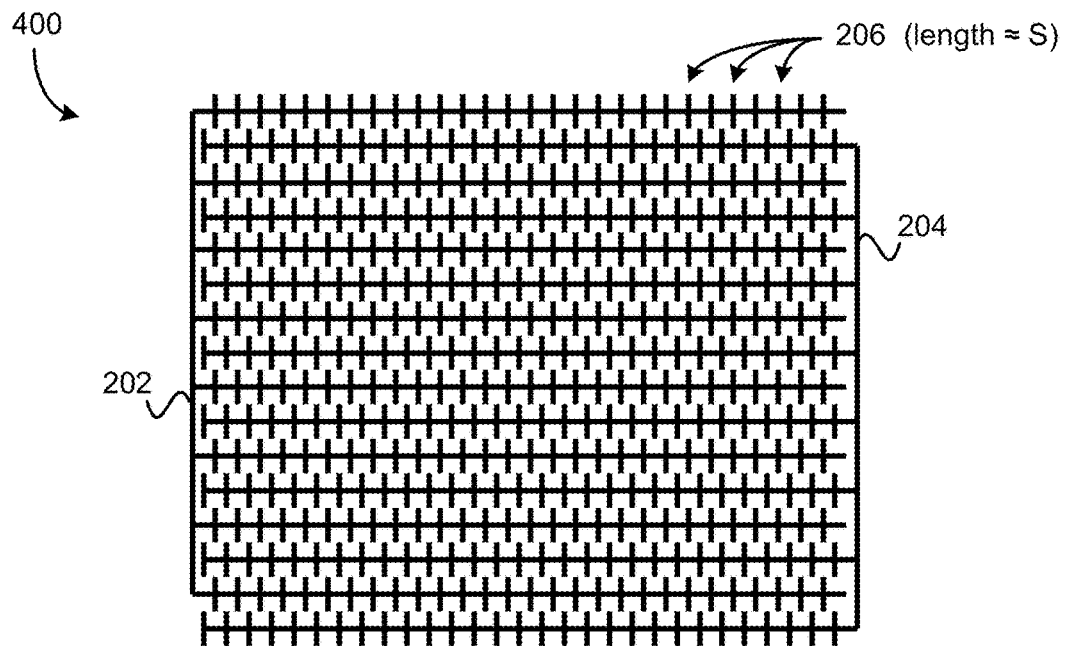
FIGS. 4A-4B are simplified schematics of IDEs having a fractal geometry, according to several exemplary embodiments.
Figure 4B:
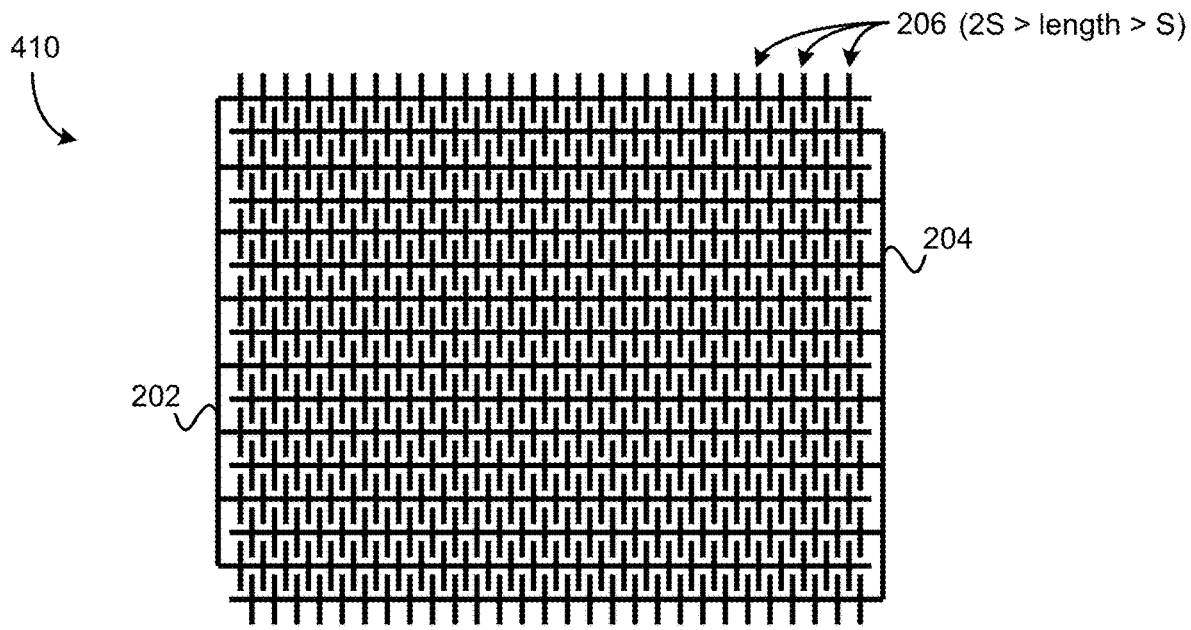

FIGS. 4A-4B represent simplified schematics of IDE structures exhibiting a "fractal" geometry, according to several exemplary embodiments. As shown IDEs 400, 410 each include leads 202, 204 as in FIG. 2A, but the fingers of the IDE are characterized by a plurality of perpendicularly-oriented protrusions 206 arranged in an alternating pattern from finger-to-finger. These protrusions 206, in various embodiments, may be substantially identical in form and composition to the fingers, but represent an alternative structural arrangement that advantageously increases the active surface area of the IDE 400, 410.

FIG. 4B shows a similar arrangement of an IDE structure 410 having a fractal geometry. However, in the embodiment of FIG. 4B, the protrusions are longer in the direction perpendicular to the fingers (e.g. a length less than twice the inter-finger distance S, but greater than the inter-finger distance S, while the protrusions in the embodiment of FIG. 4A may have a length substantially equal to the inter-finger distance S).

It should be understood that the fractal geometries shown in FIGS. 4A-4B may be utilized in place of, or in combination with, the linear geometries of IDEs 200 as shown in FIGS. 2A and 3A-3C, without departing from the scope of the presently disclosed inventive concepts.

Figure 5B:
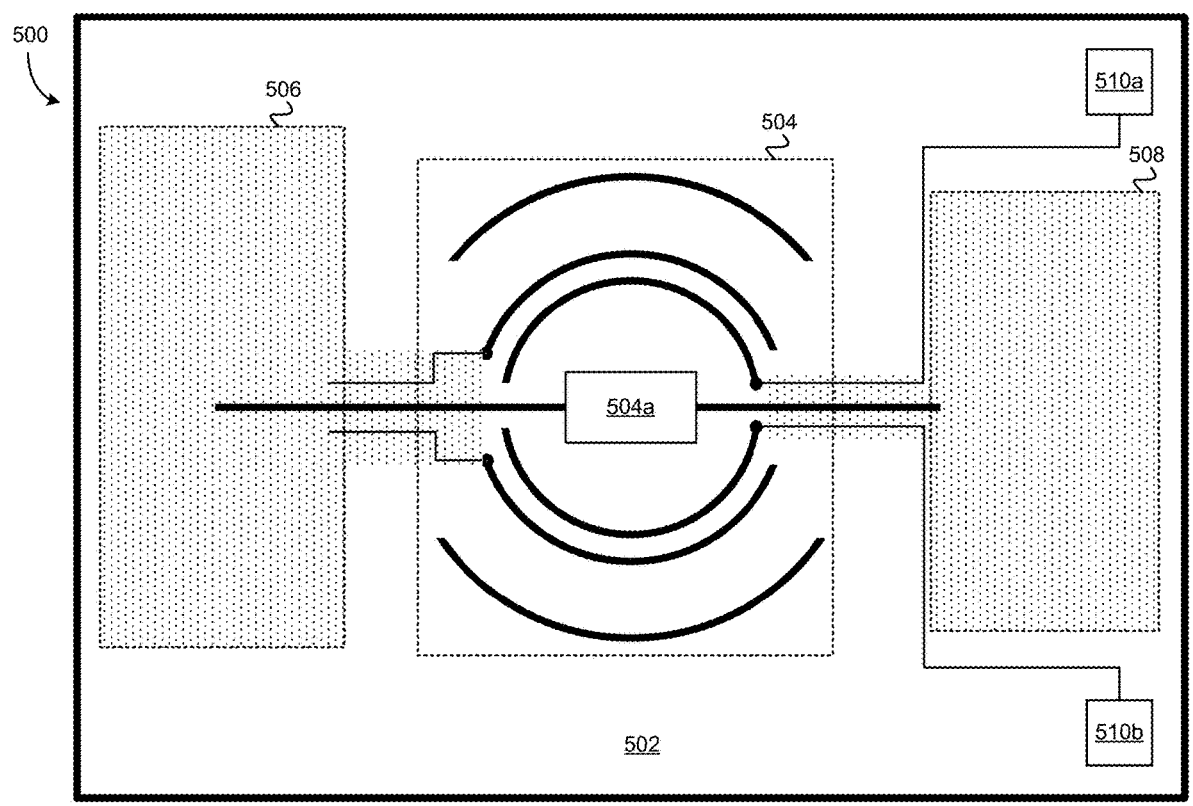
FIG. 5B is a simplified schematic of a lab-on-a-chip substrate having passivated regions formed therein/thereon, according to one embodiment.

Now with reference to FIGS. 5A-5B, an exemplary system 500 for simultaneously measuring electrophysiological responses, contractility responses, and/or morphological/growth characteristics using optical means is shown, according to one embodiment. The system 500 includes a substrate 502 having disposed therein/thereon a plurality of elements such as electrodes, contacts, leads, sensor array(s), etc. as shown and described herein.

As shown in FIG. 5A, system 500 features three regions 504, 506, and 508. Central region 504 includes the sensor array 504a, which may take any configuration and include any of the geometries A-F as shown in FIGS. 2A-4B and/or described herein. On opposing sides of the central region 504 are two Omnetics connector regions 506, 508.

Region 504 also includes a plurality of electrodes, each electrode being configured to deliver and/or receive electrical signals to/from the central region 504, and preferably to/from the sensor array 504a.

Regions 506, 508 each comprise a plurality of contacts configured to engage an Omnetics connector and electrically coupled to one or more elements (e.g. IDEs or MEA electrodes) of the sensor array 504a. For instance, as shown in FIG. 5A the various MEA electrodes of the sensor array 504a are electrically coupled to the contacts of region 506 (also referred to as a "first Omnetics connector region") via MEA leads 512, while the various IDEs of the sensor array 504a are electrically coupled to the contacts of region 508 (also referred to as a "second Omnetics connector region") via IDE leads 514.

Region 506 also includes a ground contact GND and electrophysiological stimulation contact STIM respectively and electrically coupled to the electrophysiological ground electrode 504c and electrophysiological stimulation electrode 504b of region 504 via leads.

As shown in FIG. 5A, region 506 includes sixteen Omnetics connector contacts (striped boxes), one for each of the electrodes of the MEA of sensor array 504a. Of course, in other embodiments and according to other geometries, a different number of Omnetics connector contacts may be included in region 506, preferably maintaining a 1:1 correspondence between the number of Omnetics connector contacts of region 506 and MEA electrodes of sensor array 504a. In various approaches, the contacts of region 506 may be electrically coupled to the sensor array 504 individually or in series.

Region 508 similarly includes a plurality of Omnetics connector contacts (cross-hatched boxes), which may also be electrically coupled to the sensor array 504a via leads individually or in series.

The contacts of regions 506, 508 are preferably arranged and comprised of materials in a manner suitable for engaging an Omnetics connector and facilitating control and measurement of electrical signals within the system 500, particularly measurement of electrical signals originating from tissue culture placed in proximity to the sensor array 504a, e.g. in a tissue culture chamber 112 placed on or above the sensor array as shown in FIG. 1 and described hereinabove.

Control and measurement of electrical signals in region 504 may be provided via external devices such as a multi-channel workstation 116, impedance analyzer 118, and/or electrical stimulator 120 such as shown in FIG. 1 and described hereinabove, or any equivalent thereof that would be appreciated by a person having ordinary skill in the art upon reading the present descriptions.

For instance, stimulation signals may be provided to the electrical stimulation electrodes 504d, 504e via a command or signal from electrical stimulator 120 delivered to the system 500 via contacts 510a, 510b. Field potentials may be observed over time, and/or electrophysiological signals delivered to the sensor array via the multi-channel workstation 116, electrically coupled to the electrophysiological ground GND and stimulation STIM contacts and electrically coupled to the MEA electrodes via the Omnetics connector 108 and MEA leads 512. Impedance signals may be received by the impedance analyzer 118 via the IDEs of the sensor array 504a and IDE leads 514 connecting the IDEs to the Omnetics connector contacts of Omnetics connector 110.

In general, the electrodes (e.g. electrodes of the MEA and IDEs of the sensor array 504a, stimulation electrode 504b, ground electrode 504c, stimulation electrodes 504d, 504e, etc.), contacts (e.g. Omnetics connector contacts (hashed boxes in regions 504 and 506), ground and stimulation contacts 510a, 510b, etc.) and leads (e.g. MEA leads 512, and IDE leads 514) of the system 500 may be formed from any suitable material, preferably one or more of titanium, gold, platinum, platinum black, titanium nitride, and carbon nanotube materials. In particularly preferred approaches, the electrodes and/or leads of system 500 comprise one or more of Ti/Au, Ti/Pt, Ti/Pt black, Ti/Au/Pt black, and Ti/Au/carbon nanotube materials.

The substrate 502 may comprise any suitable material that would be appreciated by a skilled artisan reading the instant descriptions, and preferably includes an optically transparent insulator material, such as glass, silicon (optionally coated on surface(s) thereof with a material such as silica or silicon nitride), or polydimethylsiloxane (PDMS), in various embodiments.

FIG. 5B is a simplified view of an upper surface of substrate 502, particularly showing regions where a passivating layer or film (indicated by stippling in the vicinity of regions 506, 508 and portions where leads connect regions 506 and 508 to region 504, respectively) may be formed to prevent corrosion and reduce interference on measurements of electrophysiological and/or contractility responses, in various embodiments. The passivating layer may be formed of any suitable material known to persons having ordinary skill in the art, and in one embodiment comprises a thin film of polyimide formed on the substrate surface using known techniques.

Accordingly, in a preferred embodiment, the presently disclosed inventive concepts include a sensor array, and systems incorporating such sensor array to facilitate the simultaneous measurement of electrophysiological and contractility responses of a tissue.

In one embodiment, the sensor array includes: a substrate; a multi-electrode array (MEA) disposed in or on the substrate; and a plurality of interdigitized electrodes (IDEs) disposed in or on the substrate. The MEA and the IDEs are interpenetrating within a plane substantially parallel to an upper surface of the substrate.

The MEA may optionally include a plurality of electrodes arranged in a coplanar grid defining a two-dimensional map of field potential-sensitive regions of the sensor array, in one embodiment.

In another embodiment, the plurality of IDEs may be interleaved with electrodes of the MEA, forming a series of alternating finger-like structures each respectively comprising either electrodes of the MEA or one or more of the IDEs.

In yet another embodiment, the IDEs may be characterized by a substantially fractal geometry.

The MEA may include sixteen electrodes arranged into four finger-like structures of four electrodes each, in a preferred configuration, while the sensor array may include at least three, and no more than nine, IDEs arranged into up to five finger-like structures each comprising one to three of the IDEs. Advantageously, the finger-like structures of the MEA and the finger-like structures comprising the IDE(s) may be arranged in an alternating pattern forming a substantially rectangular grid within the plane substantially parallel to the upper surface of the substrate.

In still yet another embodiment, the electrodes of the IDEs and electrodes of the MEA may each respectively comprise one or more materials selected from a group consisting of: titanium, gold, platinum, platinum black, and carbon nanotubes.

The substrate, in some embodiments, may include a material selected from a group consisting of: glass, silicon, polydimethylsiloxane (PDMS); and an optional coating including a material selected from a group consisting of silicon oxide and silicon nitride.

In further embodiments, the sensor array may be characterized by an area less than or equal to an area of a single well of a standard, commercially available 96-well cell culture plate, e.g. an area in a range of approximately 1-75 $mm^2$, with several examples described above regarding geometries A-D. In more embodiments, for example, intermediate between those of geometries A-C and D as described above, the MEA may have dimensions of approximately 3 mm by approximately 3 mm, and an area of approximately 9 $mm^2$. According to geometries A and B, the IDEs fit generally within this structure and so the overall area of the sensor array may be in a range from approximately 10-15 $mm^2$, in one approach.

The electrodes of the MEA and electrodes of the IDEs, in one implementation, may be characterized by sufficient spacing therebetween to permit optical investigation of a tissue disposed on the substrate in a region coinciding with the sensor array. In various embodiments, the spacing between elements of the sensor array may be at least about 20 microns, at least about 50 microns, at least about 100 microns, or combinations thereof. The spacing between the elements of the sensor array is most preferably a value approximately equal to or greater than an average diameter of the biological units (e.g. CM cells) to be optically observed within the chamber including the sensor array, e.g. cell culture chamber 112 as shown in FIG. 1.

Turning now to an exemplary embodiment of a system for simultaneously measuring electrophysiological responses and contractility responses of a tissue, in a preferred embodiment the system includes: a sensor array including a substrate; a multi-electrode array (MEA) disposed in or on the substrate; and a plurality of interdigitized electrodes (IDEs) disposed in or on the substrate. The MEA and the IDEs are interpenetrating within a plane substantially parallel to an upper surface of the substrate. The system further includes a first set of Omnetics connectors disposed in or on a surface of the substrate along one side of the substrate and electrically coupled to the sensor array via a plurality of MEA leads; a second set of Omnetics connectors disposed in or on a surface of the substrate along an opposing side of the substrate as the first set of Omnetics connectors and electrically coupled to the sensor array via a plurality of IDE leads; a cell culture chamber; and an enclosure surrounding the sensor array, the first and second sets of Omnetics connectors, and the cell culture chamber.

In preferred embodiments, the enclosure comprises a faraday cage.

The system may also include one or more external devices coupled to the system, such as an optical microscope and an objective lens positioned on opposing sides of the enclosure; where the optical microscope illuminates tissue in the cell culture chamber; and the objective lens captures light from the illuminated tissue.

Additional and/or alternative external devices may include an impedance analyzer and an electrical stimulator each electrically coupled to the sensor array via the second set of Omnetics connectors, in accordance with one embodiment.

The system may also include a plurality of electrical stimulation electrodes electrically coupled to the electrical stimulator via the second set of Omnetics connectors, in one approach.

Additional and/or alternative external devices may include a multi-channel workstation electrically coupled to the sensor array via the first set of Omnetics connectors, in yet another approach.

The system may still further include an electrophysiological ground electrode and an electrophysiological stimulation electrode each electrically coupled to the multi-channel workstation via the first set of Omnetics connectors, in various embodiments.

Preferably, a passivation layer is formed in or on one or more regions of the upper surface of the substrate that comprise and/or are proximate to: the first set of Omnetics connectors, the second set of Omnetics connectors; one or more MEA leads between the electrodes of the MEA of the sensor array and the first set of Omnetics connectors; and/or one or more IDE leads between the IDEs of the sensor array and the second set of Omnetics connectors.

In Use

Figure 8:
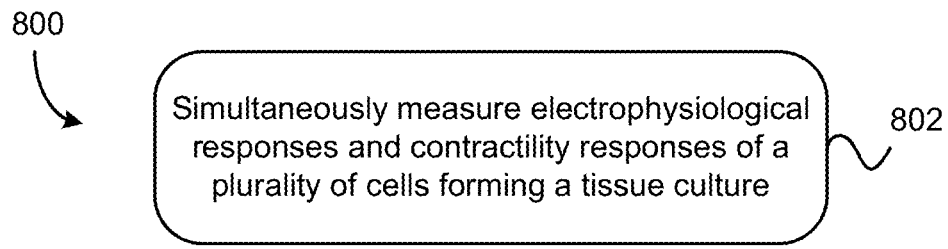
FIG. 8 is a flowchart of a method, according to one embodiment of the presently disclosed inventive concepts.

Referring now to FIG. 8, a method 800 is shown, according to one embodiment. The method 800 as presented herein may be carried out in any desired environment that would be appreciated as suitable by a person having ordinary skill in the art upon reading the present disclosure. The method 800 as presented herein may be carried out in any desired environment that would be appreciated as suitable by a person having ordinary skill in the art upon reading the present disclosure, including those of FIGS. 1-5B, in various approaches. Moreover, more or less operations than those shown in FIG. 8 may be included in method 800, according to various embodiments.

More specifically, method 800 includes simultaneously measuring electrophysiological responses and contractility responses of a plurality of cells forming a tissue culture in operation 802. Notably, the simultaneous measurement is performed using a system as described herein, preferably a system including at least a sensor array; a first set of Omnetics connectors disposed in or on a surface of the substrate along one side of the substrate and electrically coupled to the sensor array via a plurality of MEA leads; a second set of Omnetics connectors disposed in or on a surface of the substrate along an opposing side of the substrate as the first set of Omnetics connectors and electrically coupled to the sensor array via a plurality of IDE leads; a cell culture chamber; and an enclosure surrounding the sensor array, the first and second sets of Omnetics connectors, and the cell culture chamber. The sensor array, in turn, includes a substrate; a multi-electrode array (MEA) disposed in or on the substrate; and a plurality of interdigitized electrodes (IDEs) disposed in or on the substrate. The MEA and the IDEs are interpenetrating within a plane substantially parallel to an upper surface of the substrate.

Optionally, method 800 may also include optically observing a morphology of the plurality of cells of the tissue culture simultaneous to measuring the electrophysiological responses and contractility responses of the tissue culture, and/or mapping the electrophysiological responses and contractility responses in two-dimensions across the sensor array, as described elsewhere herein.

Any of the measurements/observations performed in the context of method 800 may be performed in the presence or absence of a drug of interest, to facilitate drug discovery and toxicity studies in a high-throughput and comprehensive manner.

Fabrication

In one embodiment, both the MEA and IDE microelectrodes were patterned on substrate (e.g. glass, silicon, polydimethylsiloxane (PDMS)) using standard photolithography and electron beam evaporation (Ti/Au=20 nm/250 nm). Leads to the round electrodes in the MEA were passivated with a polyimide layer, and the MEA pads were subsequently electroplated with platinum black to reduce baseline impedance. The 18-terminal Omnetics connectors were aligned with a flip-chip bonder and attached to the glass slide with silver epoxy and encapsulated in EPOTEK® 301 epoxy to protect connections from damage and moisture. A polystyrene cloning cylinder (SCIENCEWARE® cloning cylinders, Sigma-Aldrich, St Louis, MO) was glued around the circumferential edge of the base to serve as the cell culture chamber. Custom Teflon caps with a fluorinated ethylene propylene membrane were assembled and placed over each cell culture chamber to prevent evaporation of media and maintain sterility.

Figure 9:
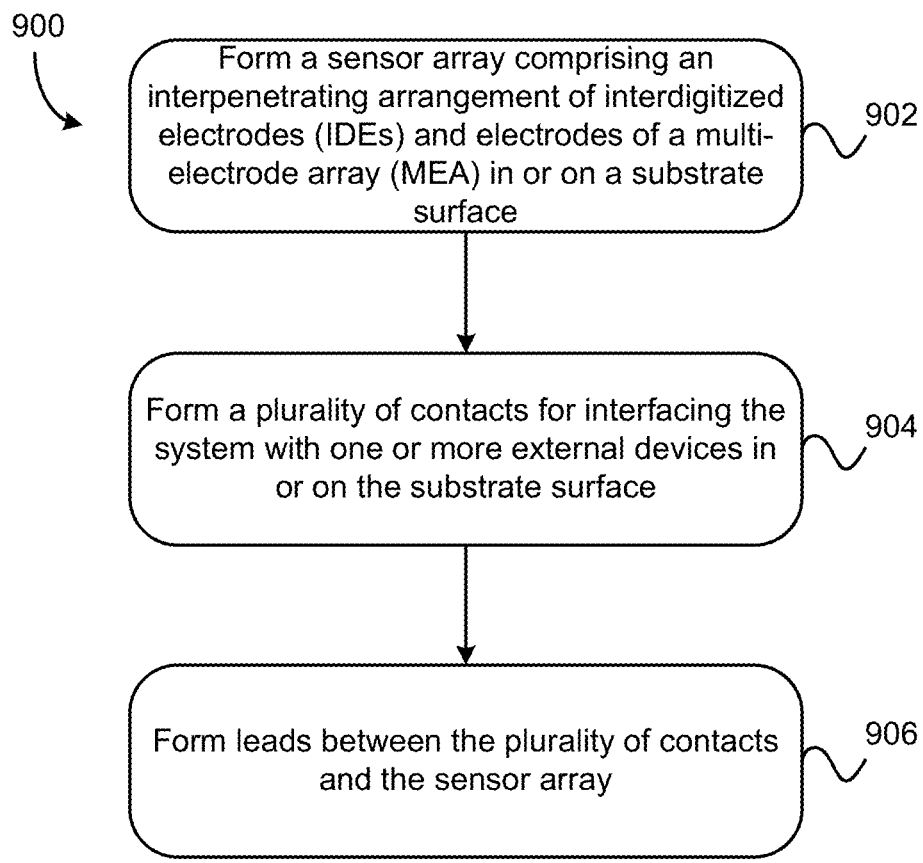
FIG. 9 is a flowchart of a method, according to one embodiment of the presently disclosed inventive concepts.

Accordingly, and with reference to FIG. 9, a method 900 of forming a system for simultaneously measuring electrophysiological responses and contractility responses of a tissue is shown, according to one embodiment. The method 900 as presented herein may be carried out in any desired environment that would be appreciated as suitable by a person having ordinary skill in the art upon reading the present disclosure, including those of FIGS. 1-5B, in various approaches. Moreover, more or less operations than those shown in FIG. 9 may be included in method 900, according to various embodiments.

More specifically, method 900 includes forming an interpenetrating arrangement of interdigitized electrodes (IDEs) and electrodes of a multi-electrode array (MEA) in or on a substrate surface in operation 902. The formation process may involve forming thin films in or on the substrate surface, e.g. via standard photolithography, electron beam evaporation, or a combination thereof, in several embodiments.

Optionally, method 900 may include passivating the electrodes of the MEA with a polyimide layer and/or electroplating the electrodes of the MEA with a suitable material to reduce impedance, such as platinum black.

Method 900 also includes operation 904, in which a plurality of contacts for interfacing the system with one or more external devices are formed in or on the substrate surface. The contacts may include any of the contacts described hereinabove, and preferably include at least the contacts for interfacing with Omnetics connectors, electrophysiological ground and stimulation electrodes 504b, 504c and electrical stimulation electrodes 504d, 504e. In one embodiment, forming the contacts comprises affixing the contacts to the substrate surface with a silver epoxy, and encapsulating the contacts in a corrosion-resistant and moisture-resistant epoxy.

In operation 906, method 900 includes forming leads between the contacts and the sensor array. Preferably, the leads are formed between individual ones of the contacts and individual ones (or groups) of the electrodes of the sensor array. More preferably, each of the electrodes of the MEA is individually connected via a lead to one of the contacts, and either each of the IDEs are individually connected via a lead to one of the contacts or the IDEs are connected in series to a plurality of the contacts. Most preferably, the electrodes of the MEA are connected to contacts on one side of the substrate, while the IDEs are connected to a different set of contacts located on an opposing side of the substrate. As for the sensor array, forming the leads may involve either or both of standard photolithography and electron beam evaporation.

The electrodes, leads, and contacts may be formed using any suitable techniques and/or materials as described herein, as well as equivalents thereof that would be appreciated by a person having ordinary skill in the art upon reading the present descriptions. In preferred approaches, the thin films of the leads and/or electrodes are characterized by a thickness in a range from approximately 20 nm to approximately 250 nm, and comprise Ti/Au.

Experimental Results

The following descriptions set forth the materials and methodologies used in several exemplary experimental investigations referenced hereinabove and/or in addition to those referenced hereinabove, using the presently disclosed inventive concepts as shown and described in FIGS. 1-5B and 8-9. It should be understood that the following descriptions are provided by way of illustration, and are not to be construed as limiting on the scope of the inventive embodiments presented above.

Human iPS-CMs were purchased from Cellular Dynamics International (Madison, WI). Cells were stored in liquid nitrogen before use. Prior to cell seeding, device culture chambers were sterilized with 70% ethanol, rinsed with autoclaved water, then incubated overnight with 40 m/mL fibronectin (Sigma-Aldrich, St Louis, MO) at 37° C. Cells were seeded at a density of 120K cells/cm2 and kept in an incubator at 37° C. and 5% CO2. Media was exchanged 4 hrs after seeding, then every 48 hours subsequently.

The MEA was connected via Omnetics connectors to an AlphaLab SnR multi-channel recording system (Alpha Omega, Alpharetta, GA) to record voltages as a function of time across all 16 electrodes of the MEA. Offline analysis of temporal differences between the 16 electrodes when voltage spikes occur generates an activation map. The activation map illustrates FP spatial propagation in the cardiac tissue monolayer across the surface area of the device.

For measuring cell adhesion and growth, electrochemical impedance spectra (EIS) were collected using a Bio-Logic SP-300 Potentiostat (Bio-Logic Science Instruments, Knoxville, TN). To characterize the quality of each set of fabricated IDEs (with no cells attached), impedance was measured inside a 100 µS/cm conductivity standard solution (Alfa Aesar, Reston, VA) across a frequency range of 100 Hz through 3 MHz with a 10-mV oscillation amplitude under open circuit conditions using Bio-Logic EC-Lab software.

For measuring cardiac contraction, high-speed impedance time recording was performed using a Keysight E4990A Impedance Analyzer (Keysight Technologies Inc., Santa Rosa, CA) and controlled using custom LabVIEW software (National Instruments, Austin, TX). For each device, impedance was measured at multiple frequencies between 5 kHz and 200 kHz to determine the frequency range that gives the highest signal-to-noise ratio.

Norepinephrine and blebbistatin were purchased from Sigma-Aldrich (St Louis, MO, USA). Both drugs were dissolved in 0.1% dimethyl sulfoxide and stored at −20° C. Drugs were diluted to desired concentrations in cell media immediately before use. Prior to drug exposure, pre-drug electrophysiology and contraction data of the cardiac tissues on a device were collected for five minutes. Next, cell media was removed from the chamber on the device, drug was added and device was incubated at 37° C. and 5% CO2 for 15 minutes. Recording was again started with the drug. Afterwards, the drug solution was removed and the culture chamber was rinsed three times with cell media, incubated at 37° C. and 5% CO2 for another 15 minutes before performing drug wash-out measurements.

Cells were fixed in 4% paraformaldehyde at 4° C. overnight, then rinsed with phosphate-buffered saline (PBS) solution. Immunostaining was performed starting with permeablizing tissues in PBS containing 0.2% triton X-100 then blocking with PBS containing 3% bovine serum albumin, followed by using primary anti-cardiac T-troponin and secondary goat antimouse IgG conjugated to AlexaFluor-488 dye (both from Thermo Fischer Scientific, Waltham, MA). Nuclei were counterstained in diluted Hoechst solution. Images were taken using a Leica DMI6000 B light microscope (Leica Microsystems Inc. Buffalo Grove, IL.). For scanning electron microscope (SEM) imaging, fixed cells in PBS were sequentially dehydrated using 50, 70, 90 and 100% ethanol, then soaked in acetone and dried in an E3100 Polaron critical point dryer (Quorum Technologies, Hatfield, PA). Dried samples were sputtered with 5-nm gold prior to SEM imaging. The SEM images were collected in a JEOL-JSM-7401F field emission SEM.

To simulate cardiac models, a Paci cell model was implemented in Matlab (The MathWorks, Inc., Natick, MA, USA) using the "ode15s" coupled differential equation solver. No stimulus current was delivered, allowing spontaneous firing only, during a window of 10 sec. The effect of norepinephrine (NE) application was simulated using the same changes to target proteins used previously in human adult ventricular cell simulations. The Paci iPS model includes the "funny" current (encoded by HCN4), which is not found in ventricle, and so the β1 response required a novel definition: 2-fold increase in conductance, in accord with several experiments.

In one experiment, 16 individual cells were simulated to represent measurements from the 16 electrodes on the chip device. Cell-to-cell variability was established by altering the maximum conductance of the 14 ion channel currents/fluxes from the original Paci values (pseudo-random multiplicative factors were drawn from a normal distribution using the "randn" function in Matlab). Ten simulated chip trials were performed for each of seven different specifications of variability (standard deviation about the mean=0.01, 0.05, 0.1, 0.25, 0.333, and 0.5 corresponding to 1, 5, 10, 25, 33.3, and 50% cell-to-cell variability, respectively). Trials were repeated six times to ensure repeatability of findings.

The Initial Paci model state (resting values, used in all simulations) was as follows: $v=-0.0743340057623841$; $m=0.102953468725004$; $h=0.786926637881461$; $j=0.253943221774722$; $d=8.96088425225182e-5$; $f1=0.970411811263976$; $f2=0.999965815466749$; $fCa=0.998925296531804$; $Xr1=0.00778547011240132$;

Xr2=0.432162576531617; Xs=0.0322944866983666;
Xf=0.100615100568753; q=0.839295925773219;
r=0.00573289893326379; Nai=10.9248496211574;
Cai=1.80773974140477e-5; Ca_SR=−0.2734234751931;
and g=0.999999981028517.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A method of forming a system for simultaneously measuring electrophysiological responses and contractility responses of a tissue, the method comprising:
    forming a sensor array comprising an interpenetrating arrangement of interdigitized electrodes (IDEs) and electrodes of a multi-electrode array (MEA) in or on a substrate surface, wherein the interpenetrating arrangement is characterized by a structure comprising a plurality of rows of the IDEs and a plurality of rows of the electrodes of the MEA, wherein the rows of the IDEs and the rows of the electrodes of the MEA are arranged in alternating fashion;
    forming a plurality of contacts for interfacing the system with one or more external devices in or on the substrate surface; and
    forming leads between the plurality of contacts and the sensor array.

2. The method as recited in claim 1, wherein forming the sensor array and forming the leads each independently comprise: standard photolithography, and/or electron beam evaporation.

3. The method as recited in claim 1, comprising passivating the electrodes of the MEA with a polyimide layer.

4. The method as recited in claim 1, comprising electroplating the electrodes of the MEA with platinum black.

5. The method as recited in claim 1, wherein forming the contacts comprises affixing the contacts to the substrate surface with a silver epoxy, and the method further comprising encapsulating the contacts in a corrosion-resistant and moisture-resistant epoxy.

6. The method as recited in claim 1, comprising forming a plurality of electrodes in proximity to the sensor array, each of the electrodes being configured to deliver and/or receive electrical signals to/from the sensor array via one or more external devices connected to the system via some or all of the contacts, wherein forming the electrodes comprises one or more of standard photolithography and electron beam evaporation.

7. The method as recited in claim 1, further comprising forming a coating on the substrate, the coating comprising silicon oxide and/or silicon nitride.

8. The method as recited in claim 1, wherein the MEA and the IDEs are formed within a plane substantially parallel to an upper surface of the substrate.

9. The method as recited in claim 1, wherein the plurality of rows of the IDEs and the plurality of rows of the electrodes of the MEA form a substantially rectangular grid.

10. The method as recited in claim 1, wherein the plurality of rows of the IDEs and the plurality of rows of the electrodes of the MEA form a substantially checkerboard pattern in which:
    the IDEs spatially correspond to a first color of spaces of the checkerboard pattern; and
    the electrodes of the MEA spatially correspond to a second color of the spaces of the checkerboard pattern.

11. The method as recited in claim 1, wherein the IDEs are characterized by a substantially fractal geometry characterized by protrusions extending away from the IDEs in a direction perpendicular to a principal axis of fingers of the IDEs, and wherein the protrusions are characterized by a length that is less than about twice an inter-finger distance S measured between the fingers of the IDEs but greater than the inter-finger distance S.

12. The method as recited in claim 1, wherein the electrodes of the IDEs comprise either titanium, carbon nanotubes, or a combination of titanium and carbon nanotubes; and
    wherein the electrodes of the MEA comprise titanium, carbon nanotubes, or a combination of titanium and carbon nanotubes.

13. The method as recited in claim 1, wherein the substrate comprises a material selected from the group consisting of: glass, silicon, polydimethylsiloxane (PDMS), and combinations thereof.

14. The method as recited in claim 1, wherein the sensor array is formed such that elements of the sensor array are separated by a spacing approximately equal to or greater than an average diameter of biological units to be optically observed within the system; and
    wherein the spacing is about 100 microns or more.

15. The method as recited in claim 1, wherein the plurality of rows of the IDEs each independently comprise multiple of the IDEs.

16. The method as recited in claim 1, wherein the plurality of rows of the electrodes of the MEA each independently comprise multiple of the electrodes of the MEA.

17. The method as recited in claim 1, wherein the plurality of rows of the IDEs and the plurality of rows of the MEAs are aligned substantially parallel to one another.

18. The method as recited in claim 1, wherein the IDEs are serially connected via a subset of the leads.

* * * * *